United States Patent [19]

Effland et al.

[11] Patent Number: 4,602,028

[45] Date of Patent: Jul. 22, 1986

[54] ANTIHYPERTENSIVE 3-ARYL-1,2-BENZISOXAZOL-SULFONYL AND SULFINYLALKANOIC ACIDS

[75] Inventors: Richard C. Effland, Bridgewater; Frank A. Pierrat, Somerset, both of N.J.

[73] Assignee: Hoechst-Roussel Pharmaceuticals, Inc., Bridgewater, N.J.

[21] Appl. No.: 561,537

[22] Filed: Dec. 14, 1983

[51] Int. Cl.[4] .................... A61K 31/42; C07D 261/20
[52] U.S. Cl. ..................................... 514/379; 548/241
[58] Field of Search ................. 548/241; 424/272; 514/329

[56] References Cited

U.S. PATENT DOCUMENTS

| 4,081,554 | 3/1978 | Cragoe et al. | 424/262 |
| 4,154,840 | 5/1979 | Ondetti et al. | 424/267 |
| 4,337,261 | 6/1982 | Shutske et al. | 424/272 |

OTHER PUBLICATIONS

Shutske, et al., [(3 Aryl-1,2-Benzisoxazol-6-yl)Oxy] Acetic Acids . . . ," *J. Med. Chem.* (25) (1982), pp. 26–44.

*Primary Examiner*—Donald G. Daus
*Assistant Examiner*—G. Hendricks
*Attorney, Agent, or Firm*—Curtis, Morris & Safford

[57] ABSTRACT

Novel (1,2-benzisoxazol)sulfinylalkanoic and -sulfonylalkanoic acids and derivative compounds, methods for preparing them and methods of treatment administering compositions containing the compounds which are useful as antihypertensives.

22 Claims, No Drawings

ANTIHYPERTENSIVE 3-ARYL-1,2-BENZISOXAZOL-SULFONYL AND SULFINYLALKANOIC ACIDS

This invention relates to (1,2-benzisoxazol)sulfonylalkanoic and -sulfinylalkanoic acids and all diastereomeric and enantiomeric forms thereof and esters and related compounds which are useful as antihypertensives. The invention also relates to methods for preparing the compounds, methods for treatment with pharmaceutically acceptable effective amounts of the compounds and pharmaceutical compositions containing the compounds as an active ingredient.

Shutske et al. U.S. Pat. No. 4,337,261 describes (1,2-benzisoxazol)phenoxyacetic acids as having diuretic properties. Pending Shutske et al. U.S. patent application Ser. No. 201,083 relates to (1,2-benzisoxazol)oxy- and (1,2-benzisoxazol)thioacetic acids and describes them as being useful as diuretic, uricosuric and antihypertensive agents. The (1,2-benzisoxazol)oxy- and (1,2-benzisoxazol)thioacetic acids and their preparation are also discussed in J. Med. Chem. 25, 36–44 (1982).

The compounds of the invention are of the general formula

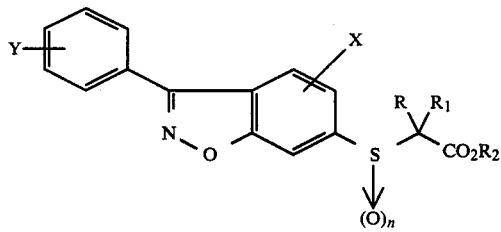

in which R, $R_1$ and $R_2$ are the same or different and each is hydrogen or lower alkyl; X and Y are the same or different and each is hydrogen, halogen or lower alkyl; and n is the integer 1 or 2. Also included within the scope of the invention are the physiologically acceptable salts of these compounds.

In the above definitions, lower alkyl means alkyl of 1 to 6 carbon atoms. Halogen means bromine, fluorine, chlorine or iodine. Preferred lower alkyls are alkyl of 1 to 3 carbon atoms and, specifically, methyl or ethyl.

The physiologically acceptable salts of the invention include, those formed with an alkali earth metal base, such as sodium, potassium or calcium salts or with a non-toxic organic base such as ethanolamine, diethanolamine or N-methylglucamine.

In addition to exhibiting antihypertensive activity, some of the compounds within the scope of the invention are also useful as intermediates for the preparation of other compounds of the invention or are useful for their hypolipidemic, diuretic, antidepressant or antiinflammatory activity.

The compounds of the invention may be prepared from the (1,2-benzisoxazol)thioacetic acids disclosed in U.S. patent application Ser. No. 201,083 and J. Med. Chem., 25, 36–44 (1982), and to the extent necessary, the disclosures of these references are hereby incorporated.

In order to obtain the compounds of the invention a (1,2-benzisoxazol)thioacetic acid or ester of the formula (I)

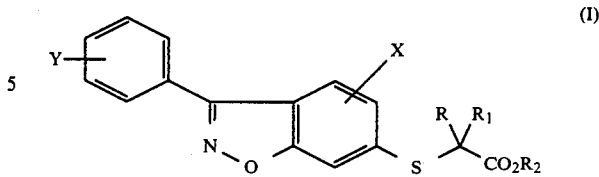

wherein R, $R_1$, $R_2$, X and Y are as defined above is treated with an oxidizing agent such as peroxide in the presence of an organic acid such as acetic acid, formic acid or trifluoroacetic acid. The reaction may be carried out with or without an inert solvent such as dichloromethane or acetone at temperatures of ambient temperature (15°–25° C.) to reflux. The reaction may be carried out for ½ to 24 hours, but typically is carried out over a period of two to four hours.

Alternatively, the sulfide starting material, that is, the (1,2-benzisoxazol)thioacetic acid or ester of the formula I, may also be oxidized in the presence of an oxidizing agent such as sodium periodate to form the compounds of the invention. The oxidation takes place preferably in the presence of a solvent, such as, methanol.

Other suitable oxidants include peracetic or perbenzoic acids or other organic "per" acids.

Generally, the reaction of the sulfide starting material under mild conditions involving lower temperatures and shorter reaction times with one equivalent of an oxidizing agent favor the formation of the sulfinyl derivatives, that is, compounds in which n is 1. More vigorous reaction conditions using higher temperatures, longer reaction times and an excess of the oxidizing agent result in further oxidation of the sulfinyl derivatives to the sulfonyl products, that is, compounds in which n is 2. The nature of the sulfide, oxidizing agent, solvent, reaction time and temperature are all factors which affect the rate of oxidation. The progress of the oxidation reaction may be monitored by a suitable analytical method, such as thin-layer or gas chromatography, to follow the appearance of the sulfinyl compound and disappearance of the sulfide starting material as well as the formation of the sulfonyl derivative from the sulfinyl compound. Other analytical methods, such as infra-red or mass spectroscopy, may also be used to monitor the reaction. By monitoring the reaction, the reaction may be controlled and stopped to produce the sulfinyl derivative, or continued to produce the sulfonyl derivative.

Esters ($R_2$ is lower alkyl) of the invention may be converted to the corresponding acetic acid ($R_2$ is hydrogen) by hydrolysis. One method involves treating the ester with sodium hydroxide and methanol at temperatures of ambient to reflux for ¼ to 4½ hours and then acidifying with hydrochloric acid.

The compounds of the invention are useful as antihypertensive agents due to their ability to depress blood pressure in mammals. Antihypertensive activity is measured in the spontaneous hypertensive rat by the indirect tail cuff method described in "Methods in Pharmacology," A. Schwartz, Ed., Vol. I, Appleton-Century Crofts, New York, New York, 1971, p. 135. In this procedure, a group of five animals is treated orally for three days with the test compound and compared to the control group of the same number. The drop in blood pressure is measured on the third day following administration. The antihypertensive activity of the compounds is set forth in Table I and is expressed as the mm decrease in mean arterial blood pressure at doses of 50 mg/kg.

TABLE I

| Compound | Decrease in Blood Pressure (mm/Hg) |
| --- | --- |
| 1. [[7-chloro-3-(2-fluorophenyl)-1,2-benzisoxazol-6-yl]sulfonyl]acetic acid | 63 |
| 2. Ethyl 2-[[3-(4-chlorophenyl)-1,2-benzisoxazol-6-yl]sulfonyl]-2-methylpropionate | 24 |
| 3. 2-[[7-chloro-3-(2-fluorophenyl)-1,2-benzisoxazol-6-yl]sulfonyl]propionic acid | 29 |
| 4. Ethyl[[3-(4-chlorophenyl)-1,2-benzisoxazol-6-yl]sulfonyl]acetate | 27 |
| 5. 2-[[3-(4-chlorophenyl)-1,2-benzisoxazol-6-yl]sulfinyl]-2-methylpropionic acid | 23 |

Blood pressure reduction is achieved when the compounds of the invention are administered to a patient requiring such treatment at an effective oral, parenteral or intravenous dose of from 0.1 to 50 mg/kg of body weight per day. A preferred effective dose within this range is from about 0.1 to 5 mg/kg of body weight per day. A particularly preferred effective amount is about 1 mg/kg body weight per day. It is to be understood, however, that for any particular patient, specific dosage regimens should be adjusted according to the individual need and the professional judgment of the person administering or supervising the administration of the compounds of the invention. It is to be further understood that the dosages set forth are examples only and that they do not, to any extent, limit the scope or practice of the invention.

Examples of some of the compounds of the invention are:

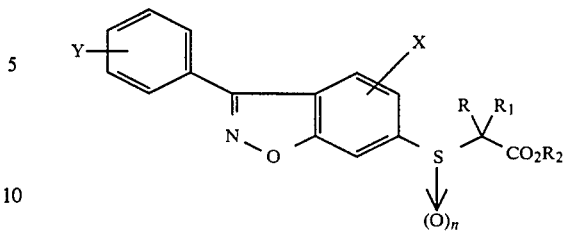

| Y | X | R | R¹ | R² | n | Name |
| --- | --- | --- | --- | --- | --- | --- |
| H | 7-CH₃ | H | H | H | 1 | [(7-methyl-3-phenyl-1,2-benzisoxazol-6-yl)sulfinyl]acetic acid |
| | | | | | 2 | [(7-methyl-3-phenyl-1,2-benzisoxazol-6-yl)sulfonyl]acetic acid |
| 4-CH₃ | 7-Cl | H | C₂H₅ | H | 1 | 2-[(7-chloro-3-(4-methylphenyl)-1,2-benzisoxazol-6-yl)sulfinyl]butyric acid |
| 4-CH₃ | 7-Cl | H | C₂H₅ | CH₃ | 1 | Methyl 2-[(7-chloro-3-(4-methylphenyl)-1,2-benzisoxazol-6-yl)sulfinyl]butyrate |
| 4-CH₃ | 7-Cl | H | C₂H₅ | CH₃ | 2 | Methyl 2-[(7-chloro-3-(4-methylphenyl)-1,2-benzisoxazol-6-yl)sulfonyl]butyrate |
| 4-CH₃ | 7-Cl | H | C₂H₅ | H | 2 | 2-[(7-chloro-3-(4-methylphenyl)-1,2-benzisoxazol-6-yl)sulfonyl]butyric acid |
| 4-Br | 7-Cl | H | CH₃ | H | 1 | 2-[(3-(4-bromophenyl)-7-chloro)-1,2-benzisoxazol-6-yl)sulfinyl]propionic acid |
| 4-Br | 7-Cl | H | CH₃ | H | 2 | 2-[(3-(4-bromophenyl)-7-chloro)-1,2-benzisoxazol-6-yl)sulfonyl]propionic acid |

Effective amounts of the compounds of the present invention may be administered to a patient by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0-300 milligrams of a compound of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed. All temperatures are given in degrees centigrade.

EXAMPLE 1

Ethyl[[7-chloro-3-(2-fluorophenyl)-1,2-benzisoxazol-6-yl]sulfinyl]acetate

A mixture of 3.0g (8.2 mmole) of ethyl[[7-chloro-3-(2-fluorophenyl)-1,2-benzisoxazol-6-yl]thio]acetate, 2.5g of a 30% $H_2O_2$ solution, 10 ml of formic acid and 50 ml of $CH_2Cl_2$ was stirred at room temperature for two hours. The reaction was diluted with water and extracted three times with $CH_2Cl_2$. The organics were combined, washed with dilute $NaHCO_3$ and dried over $MgSO_4$. The solution was concentrated at reduced pressure to a yellow oil which solidified to a cream-colored solid, 3.0g (94%) of ethyl[[7-chloro-3-(2-fluorophenyl)-1,2-benzisoxazol-6-yl]sulfinyl]acetate, m.p. 115°–118° C. The solid was recrystallized from ether to afford pale yellow prisms of ethyl[[7-chloro-3-(2-fluorophenyl)-1,2-benzisoxazol-6-yl]sulfinyl]acetate, m.p. 120°–121° C.

Analysis: Calculated for $C_{17}H_{13}ClFNO_4S$:53.48% C, 3.43% H. Found:53.24% C, 3.43% H.

EXAMPLE 2

2-[[3-(4-chlorophenyl)-1,2-benzisoxazol-6-yl]sulfonyl]-2-methylpropionic acid 3.70g (9.10 mmol) of ethyl 2-[[3-(4-chlorophenyl)1,2-benzisoxazol-6-yl]sulfonyl]-2-methylpropionate was combined with 50 ml of methanol in a flask. The mixture was heated to reflux and an excess (50 ml) of 10% NaOH was added. Initially after the addition, the solution was clear yellow but after a few minutes a precipitate began to form. After refluxing for about one hour, the mixture was cooled and acidified with dilute HCl. The precipitate was collected and recrystallized from methanol to yield 3.27 g of 2-[[3-(4-chlorophenyl)-1,2-benzisoxazol-6-yl]sulfonyl]-2-methylpropionic acid, m.p. 235°–239° C., with decomposition.

Analysis: Calculated for $C_{17}H_{14}ClNO_5S$:53.8% C, 3.7% H. Found:53.36% C, 3.74% H.

EXAMPLE 3

Ethyl 2-[[3-(4-chlorophenyl)-1,2-benzisoxazol-6-yl)]sulfonyl]-2-methylpropionate 3.0 g (8.0 mmole) of ethyl 2-[[3-(4-chlorophenyl)-1,2-benzisoxazol-6-yl)]thio-2-methylpropionate and 10 ml of formic acid were combined in a flask with 50 ml of dichloromethane and an excess (10 ml) of 30% $H_2O_2$. The reaction was briskly stirred overnight, diluted with water and the layers separated. The organic layer was washed several times with dilute acid, a saturated sodium bicarbonate solution, and a saturated salt solution, followed by drying over sodium sulfate. The dichloromethane was evaporated to an oil which solidified and was recrystallized from methanol to obtain white crystals, 2.56 g (82%) of ethyl 2-[[3-(4-chlorophenyl)-1,2-benzisoxazol-6-yl)]sulfonyl]-2-methylpropionate, m.p. 123°–124° C.

Analysis: Calculated for $C_{19}H_{18}ClNO_5S$: 56.0% C, 4.4% H. Found: 56.01% C, 4.43% H.

EXAMPLE 4

2-[[3-(4-chlorophenyl)-1,2-benzisoxazol-6-yl]sulfinyl]-2-methylpropionic acid 5.56 g (16.0 mmol) of 2-[[3-(4-chlorophenyl)-1,2-benzisoxazol-6-yl]thio]-2-methylpropionic acid and 6 ml of 30% $H_2O_2$ were combined in 200 ml glacial acetic acid. The mixture was stirred at room temperature and monitored by TLC for the disappearance of starting material and the appearance of product. After about four hours the reaction was stopped by diluting with excess 3N HCl. The resulting precipitate was filtered and washed several times with cold toluene to yield white crystals, 3.38 g (58%) of 2-[[3-(4-chlorophenyl)-1,2-benzisoxazol-6-yl]sulfinyl]-2-methylpropionic acid, m.p. 184°–185° C.

Analysis: Calculated for $C_{17}H_{14}ClNO_4S$: 56.1% C, 3.9% H. Found: 56.03% C, 3.94% H.

EXAMPLE 5

[[3-(4-chlorophenyl)-1,2-benzisoxazol-6-yl]sulfonyl]acetic acid 3.1 g (8.17 mmol) of ethyl[[3-(4-chlorophenyl)-1,2-benzisoxazol-6-yl]sulfonylacetate was dissolved in 50 ml of methanol and an excess (15 ml) of 10% NaOH solution (15 ml) was added. The solution was refluxed for 15 minutes, cooled and acidified with 3N HCl. The white precipitate which formed was collected and recrystallized from 1:1 ethanol/water to give white crystals, 2.23 g (78%) of [[3-(4-chlorophenyl)-1,2-benzisoxazol-6-yl]sulfonyl]acetic acid, m.p. 201°–203° C.

Analysis: Calculated for $C_{15}H_{10}ClNO_5S$: 51.2% C, 2.8% H. Found: 51.05%, 2.89% H.

EXAMPLE 6 a.

Ethyl[[3-(2-fluorophenyl)-1,2-benzisoxazol-6-yl]sulfinyl]acetate 3.0 g (9.06 mmol) of ethyl[3-(2-fluorophenyl)-1,2-benzisoxazol-6-yl]thioacetate was stirred in 10 ml of formic acid, 50 ml of dichloromethane and 5 ml of a 30% $H_2O_2$ solution at room temperature. The reaction progress was monitored by gas chromatography. After 30 minutes, the reaction mixture was worked up by separating the layers and washing the dichloromethane layer twice with water and then with a saturated sodium chloride solution. After drying over sodium sulfate, the solvent was evaporated to provide 3.2 g of ethyl[[3-(2-fluorophenyl)-1,2-benzisoxazol-6-yl]sulfinyl]acetate. The structure was confirmed by infra-red and mass spectroscopy.

b.
[[3-(2-fluorophenyl)-1,2-benzisoxazol-6-yl]sulfinyl]acetic acid 3.14 of crude ethyl[[3-(2-fluorophenyl)-1,2-benzisoxazol-6-yl]sulfinyl]acetate from Example 6a was added to 100 ml of 1:1 10% NaOH/MeOH. The solution was stirred at ambient temperature for ½ hour and a white precipitate formed. The mixture was poured into an excess crushed ice/concentrated HCl mixture and the resulting precipitate was filtered. The white residue was recrystallized from 1:4 ethyl acetate/hexanes to afford white crystals, 1.86 g (64% based on the thioacetate) of [[3-(2-fluorophenyl)-1,2-benzisoxazol-6-yl]sulfinyl]acetic acid, m.p. 165°–166° C.

Analysis: Calculated for $C_{15}H_{10}FNO_4S$: 56.4% C, 3.1% H. Found: 56.00% C, 3.18% H.

EXAMPLE 7 a.
Ethyl[[3-(2-fluorophenyl)-1,2-benzisoxazol-6-yl]sulfonyl]acetate

A mixture of 3.0 g (9.06 mmol) of ethyl[3-(2-fluorophenyl)-1,2-benzisoxazol-6-yl]thioacetate in 10 ml of formic acid, 50 ml of dichloromethane and 5 ml of a 30% $H_2O_2$ solution was stirred vigorously at room temperature. The progress of the reaction was monitored by gas chromatography. The sulfinyl compound of Example 6a formed initially, but the reaction was continued overnight to give essentially complete conversion to the desired sulfonyl product. The reaction mixture was worked up by separating the layers and washing the dichloromethane layer with water and then with a saturated sodium chloride solution. After drying over magnesium sulfate, the dichloromethane was evaporated to provide 3.1 g (94%) of ethyl[3-(2-fluorophenyl)-1,2-benzisoxazol-6-yl]sulfonyl]acetate. The structure was confirmed by infra-red and mass spectroscopy.

b.
[[3-(2-fluorophenyl)-1,2-benzisoxazol-6-yl]sulfonyl]acetic acid

Ethyl[[3-(2-fluorophenyl)-1,2-benzisoxazol-6-yl]sulfonyl]acetate, prepared from 3.00 g of ethyl[[3-(2-fluorophenyl)-1,2-benzisoxazol-6-yl]thio]acetate, was added to 100 ml of a 1:1 methanol/10% sodium hydroxide solution. The solution was stirred and within a few minutes a white precipitate appeared. The reaction mixture was stirred for 15 minutes and then poured into an excess ice/concentrated HCl mixture. The precipitate was collected and recrystallized from 1:1 ethanol/water to yield white crystals, 2.10 g (70% based on the thio acetate) of [[3-(2-fluorophenyl)-1,2-benzisoxazol-6-yl]sulfonyl]acetic acid, m.p. 168°–169° C.

Analysis: Calculated for $C_{15}H_{10}FNO_5S$: 53.7% C, 3.0% H. Found: 53.84% C, 3.08% H.

EXAMPLE 8

[[5-bromo-3-(2-fluorophenyl)-1,2-benzisoxazol-6-yl]sulfonyl]acetic acid 2.93 g (7.67 mmol) of [[5-bromo-3-(2-fluorophenyl)-1,2-benzisoxazol-6-yl]thio]acetic acid was dissolved in 50 ml of trifluoroacetic acid and an excess (8 ml) 30% $H_2O_2$ was added. The solution was stirred at ambient temperature for four hours and then poured into excess water. The white precipitate which formed was filtered, recrystallized from 1:1 ethanol/water and dried under vacuum at 80° C to afford beige needles, 2.10g (66%) of [[5-bromo-3-(2-fluorophenyl)-1,2-benzisoxazol-6-yl]sulfonyl]acetic acid, m.p. 200° C., with decomposition.

Analysis: Calculated for $C_{15}H_9BrFNO_5S$: 43.5% C, 2.2% H. Found: 43.65% C, 2.12% H.

EXAMPLE 9

[[5-bromo-3-(2-fluorophenyl)-1,2-benzisoxazol-6-yl]sulfinyl]acetic acid 2.8 g (7.33 mmol) of [[5-bromo-3-(2-fluorophenyl)-1,2-benzisoxazol-6-yl]thio]acetic acid was combined with 30 ml (2 eq.) of 0.5M sodium periodate solution in 300 ml of 4:1 methanol/water. The mixture was refluxed for 18 hours during which the insoluble sodium iodate precipitated. The reaction mixture was then poured into excess 3N HCl and extracted several times with ethyl acetate. The ethyl acetate extracts were combined, washed with water and a saturated salt solution, dried over magnesium sulfate, filtered and evaporated to yield a white solid. The solid was triturated with hexanes and dried under vacuum to yield 2.51 g (86%) of [[5-bromo-3-(2-fluorophenyl)-1,2-benzisoxazol-6-yl]sulfinyl]acetic acid, m.p. 173°–174° C.

Analysis: Calculated for $C_{15}H_9BrFNO_4S$: 45.2% C, 2.3% H, 3.5% N. Found: 45.36% C, 2.32% H, 3.42% N.

EXAMPLE 10

2-[[3-(2-fluorophenyl)-1,2-benzisoxazol-6-yl]sulfonyl] propionic acid 2.12 g (6.69 mmol) of 2-[[3-(2-fluorophenyl)-1,2-benzisoxazol-6-yl]thio] propionic acid, 7 ml of trifluoroacetic acid, and 4 ml of a 30% $H_2O_2$ solution were combined in 50 ml of dichloromethane. The biphasic solution was stirred for three hours at ambient temperature and then diluted with water. The organic layer was separated and the aqueous layer was extracted with ethyl acetate. The organics were combined, washed with water and a saturated salt solution, dried over magnesium sulfate, filtered and evaporated to yield an oil which crystallized upon the addition of hexanes. The crystals were collected and recrystallized from 1:1 dichlormethane/hexanes to yield a white powder, 1.84 g (79%) of [[3-(2-fluorophenyl)-1,2-benzisoxazol-6-yl]sulfonyl]-2-propionic acid, m.p. 142°–144° C.

Analysis: Calculated for $C_{16}H_{12}FNO_5S$: 55.0% C, 3.50% H, 4.0% N. Found: 54.86% C 3.48% H 3.94% N.

EXAMPLE 11

2-[[7-chloro-3-(4-chlorophenyl)-1,2-benzisoxazol-6-yl]sulfonyl]propionic acid 2.50 g (6.79 mmol) of 2-[[7-chloro-3-(4-chlorophenyl)-1,2-benzisoxazol-6-yl]thio]propionic acid and an excess (7 ml) 30% hydrogen peroxide solution were combined in 50 ml of trifluoroacetic acid. The solution was stirred for two hours during which time a white precipitate formed. The reaction mixture was then poured into excess water and the precipitate was collected, dried in a desiccator and recrystallized from 1:1 THF/hexanes to yield a white powder, 1.93 g (71%) of 2-[[7-chloro-3-(4-chlorophenyl)-1,2-benzisoxazol-6-yl]sulfonyl]propionic acid, m.p. 249° C., with decomposition.

Analysis: Calculated for $C_{16}H_{11}Cl_2NO_5S$: 48.0% C, 2.8% H, 3.5% N. Found: 48.15% C, 2.80% H, 3.32% N.

EXAMPLE 12

[[7-chloro-3-(4-chlorophenyl)-1,2-benzisoxazol-6-yl]sulfonyl]acetic acid 3.79 g (10.7 mmol) of [[7-chloro-3-(4-chlorophenyl)-1,2-benzisoxazol-6-yl]thio]acetic acid and an excess (10 ml) of 30% $H_2O_2$ were combined in 50 ml of trifluoroacetic acid. The reaction solution was stirred for four hours and then poured into excess water (1:1). The precipitate which formed was filtered, dried, and passed through a column of 40 g of silica in 1% $HOAc/CH_3CN$ to remove the sulfoxide impurities. The product fractions were evaporated and the residue was recrystallized from 1:10:10 $TFAA/MeOH/H_2O$ to yield a white powder, 2.30 g (56%) of [[7-chloro-3-(4-chlorophenyl)-1,2-benzisoxazol-6-yl]sulfonyl]acetic acid, m.p. 212°–213° C.

Analysis: Calculated for $C_{15}H_{19}Cl_2NO_5S$: 46.6% C, 2.3% H, 3.6% N. Found: 47.03% C, 2.37% H, 3.70% N.

EXAMPLE 13

2-[[7-chloro-3-(4-chlorophenyl)-1,2-benzisoxazol-6-yl]sulfinyl]propionic acid 2.35 g (6.39 mmol) of 2-[[7-chloro-3-(4-chlorophenyl)-1,2-benzisoxazol-6-yl]thio]propionic acid, and 20 ml of a 1:1 mixture of formic acid and 30% $H_2O_2$ were combined in 50 ml of acetone. The resulting solution was stirred at ambient temperature for one hour during which a white precipitate formed. The reaction mixture was evaporated in vacuo to remove the acetone, then poured into excess water and filtered. The precipitate was washed with 1:1 methanol/water and dried in a vacuum desiccator to yield a white powder, 2.23 g (91%) of 2-[[7-chloro-3-(4-chlorophenyl)-1,2-benzisoxazol-6-yl]-sulfinyl]propionic 1 acid, m.p. 260° C. The $^1H$ NMR (DMSO-$d_6$): 1.11 (d, 1.5H, $CH_3$), 1.44 (d, 1.5H, $CH_3$), 4.08 (q, 1H, CH) spectrum indicated two diastereomeric forms.

Analysis: Calculated for $C_{16}H_{11}Cl_2NO_4S$: 50.0% C, 2.9% H, 3.6% N. Found: 49.93% C, 2.95% H, 3.57% N.

EXAMPLE 14

2-[[7-chloro-3-(2-fluorophenyl)-1,2-benzisoxazol-6-yl]sulfonyl]propionic acid

A solution of 3.31 g (9.41 mmol) of 2-[[7-chloro-3-(2-fluorophenyl)-1,2-benzisoxazol-6-yl]thio]propionic acid in glacial acetic acid (25 ml) was warmed to 45° C. and 4 ml of 30% $H_2O_2$ was added dropwise. After refluxing for three hours, the reaction mixture was poured over an ice/water mixture and extracted with ethyl acetate. The ethyl acetate solution was dried over $MgSO_4$ and the solvent removed to give 4.4 g of pale yellow solid. Recrystallization from ethyl acetate-chloroform gave an off-white solid, 2.05 g (57%) of 2-[[7-chloro-3-(2-fluorophenyl)-1,2-benzisoxazol-6-yl]sulfonyl]propionic acid, m.p. 220°–225° C.

Analysis: Calculated for $C_{16}H_{11}ClFNO_5S$: 50.07% C, 2.89% H, 3.65% N. Found: 49.76% C, 2.87% H, 3.52% N.

EXAMPLE 15

Ethyl 2-[[3-(4-chlorophenyl)-1,2-benzisoxazol-6yl-]sulfinyl]-2-methylpropionate 3.0 g (8.0 mmole) of ethyl 2-[[3-(4-chlorophenyl)-1,2-benzisoxazol-6-yl]thio]-2-methylpropionate was combined in a flask with 0.91 g (1 eq.) of a 30% $H_2O_2$ solution, 10 ml of formic acid and 50 ml of dichloromethane. The mixture was briskly stirred and the reaction monitored by TLC. After 45 minutes, 1 ml more of a 30% $H_2O_2$ solution was added to consume the remaining starting material. The reaction was stopped when the TLC showed the starting material was consumed (at which point oxidation of the product to the sulfone will begin) and the reaction mixture was diluted with 3N HCl. The dichloromethane layer was separated, washed with 3N HCl, water, and a saturated salt solution, dried over sodium sulfate and evaporated to an oil. The oil was crystallized by adding methanol and the resulting solid was collected and recrystallized from methanol to yield 1.6 g (52%) of ethyl 2-[[3-(4-chlorophenyl)-1,2-benzisoxazol-6yl-]sulfinyl]-2-methylpropionate, m.p. 89° C.

Analysis: Calculated for $C_{19}H_{18}ClNO_4S$: 58.3% C, 4.6% H. Found: 58.48% C, 4.59% H.

EXAMPLE 16

Ethyl[[3-(4-chlorophenyl)-1,2-benzisoxazol-6yl-]sulfonyl]acetate 3.00 g (8.63 mmol) of ethyl[[3-(4-chlorophenyl)-1,2-benzisoxazol-6-yl]thio]acetate, 50 ml of dichloromethane, 10 ml of formic acid, and an excess (6 ml) of a 30% $H_2O_2$ solution were combined in a flask. The biphasic solution was stirred overnight at ambient temperature and was then poured into 100 ml of water. The dichloromethane layer was separated and was washed twice with 3N HCl, and then with water and a saturated salt solution. The dichloromethane solution was dried over sodium sulfate and evaporated to yield a white solid which was washed with cold methanol and dried to yield 2.89 g (88%) of ethyl[[3-(4-chlorophenyl)-1,2-benzisoxazol-6-yl]sulfonyl]acetate, m.p. 151°–152° C.

Analysis: Calculated for $C_{17}H_{14}ClNO_5S$: 53.8% C, 3.7% H. Found: 53.40% C, 3 77% H.

EXAMPLE 17

Ethyl[[7-chloro-3-(2-fluorophenyl)-1,2-benzisoxazol-6-yl-]sulfonyl]acetate 2.5 ml of 30% $H_2O_2$ (22 mmol) was added dropwise to a mixture of 2 g (0.005 mole) of ethyl[[7-chloro-3-(2-fluorophenyl)-1,2-benzisoxazol-6-yl]thio]acetate and 20 ml of acetic acid. The reaction mixture was warmed to reflux and monitored by TLC. After 24 hours the reaction mixture was poured into water and ice, precipitating a white solid which was filtered, dried, and recrystallized from ether to afford 1.8 g (86%) of ethyl[[7-chloro-3-(2-fluorophenyl)-1,2-benzisoxazol-6-yl]sulfonyl]acetate, m.p. 90°–92° C.

Analysis: Calculated for $C_{17}H_{13}ClFNO_5S$: 51.32% C, 3.29% H. Found: 51.04% C, 3.32% H.

EXAMPLE 18

[[7-chloro-3-(2-fluorophenyl)-1,2-benzisoxazol-6-yl]sulfonyl]acetic acid 4.9 g (12.3 mmol) of ethyl[[7-chloro-3-(2-fluorophenyl)-1,2-benzisoxazol-6-yl]sulfonyl]acetate was added to 500 ml of methanol and 40 ml of 15% aqueous NaOH was added to the suspension. A yellow solution resulted and within 15 minutes a creamy precipitate formed. After stirring four hours at room temperature the reaction mixture was poured into an ice/dilute HCl mixture and the precipitate was filtered, dried, and recrystallized from toluene to afford a white solid, 2.5 g of [[7-chloro-3-(2-fluorophenyl)-1,2-benzisoxazol-6-yl]sulfonyl]acetic acid , m.p. 204° C.

Analysis: Calculated for $C_{15}H_9ClFNO_5S$: 48.6% C, 2.4% H. Found: 48.2% C, 2.5% H.

We claim:

1. A compound of the formula

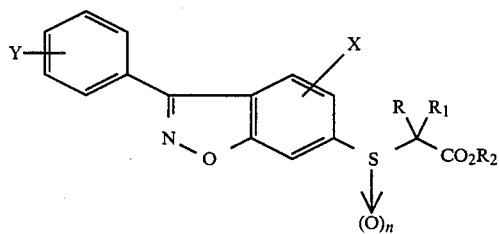

in which R, $R_1$ and $R_2$ are the same or different and each is hydrogen or lower alkyl; X and Y are the same or different and each is hydrogen, halogen or lower alkyl, n is the integer 2 and a pharmaceutically acceptable salt thereof.

2. The compound of claim 1, wherein R and $R_1$ are the same or different and each is hydrogen or methyl.

3. The compound of claim 1, wherein $R_2$ is hydrogen or ethyl.

4. The compound of claim 1, wherein X is hydrogen, chorine or bromine.

5. The compound of claim 1, wherein Y is fluorine or chlorine.

6. The compound of claim 1, wherein X is hydrogen, chlorine or bromine; Y is chlorine or fluorine; R is hydrogen or methyl; $R_1$ is hydrogen or methyl; and $R_2$ is hydrogen or ethyl.

7. The compound of claim 1 which is ethyl[[7-chloro-3-(2-fluorophenyl)-1,2-benzisoxazol-6-yl]sulfonyl]acetate.

8. The compound of claim 1 which is 2-[[3-(4-chlorophenyl)-1,2-benzisoxazol-6-yl]sulfonyl]-2-methylpropionic acid.

9. The compound of claim 1 which is ethyl 2-[[3-(4-chlorophenyl)-1,2-benzisoxazol-6-yl)]sulfonyl]-2-methylpropionate.

10. The compound of claim 1 which is [[3-(4-chlorophenyl)-1,2-benzisoxazol-6-yl]sulfonyl]acetic acid.

11. The compound of claim 1 which is ethyl[[3-(2-fluorophenyl)-1,2-benzisoxazol-6-yl]sulfonyl]acetate.

12. The compound of claim 1 which is [[3-(2-fluorophenyl)-1,2-benzisoxazol-6-yl]sulfonyl]acetic acid.

13. The compound of claim 1 which is [[5-bromo-3-(2-fluorophenyl)-1,2-benzisoxazol-6-yl]sulfonyl]acetic acid.

14. The compound of claim 1 which is 2-[[3-(2-fluorophenyl)-1,2-benzisoxazol-6-yl]sulfonyl] propionic acid.

15. The compound of claim 1 which is 2-[[7-chloro-3-(4-chlorophenyl)-1,2-benzisoxazol-6-yl]sulfonyl]propionic acid.

16. The compound of claim 1 which is [[7-chloro-3-(4-chlorophenyl)-1,2-benzisoxazol-6-yl]sulfonyl]acetic acid.

17. The compound of claim 1 which is 2-[7-chloro-3-(2-fluorophenyl)-1,2-benzisoxazol-6-yl]sulfonyl]propionic acid.

18. The compound of claim 1 which is ethyl[[3-(4-chlorophenyl)-1,2-benzisoxazol-6-yl]sulfonyl]acetate.

19. The compound of claim 1 which is ethyl[[7-chloro-3-(2-fluorophenyl)-1,2-benzisoxazol-6-yl]sulfonyl]acetate.

20. The compound of claim 1 which is [[7-chloro-3-(2-fluorophenyl)-1,2-benzisoxazol-6-yl]sulfonyl]acetic acid.

21. A pharmaceutical composition comprising a pharmaceutically effective amount of the compound claimed in claim 1.

22. A method for producing an antihypertensive effect which comprises administering to a patient in need of an antihypertensive effect an antihypertensive effective amount of a compound claimed in claim 1.

* * * * *

UNITED STATES PATENT AND TRADEMARK OFFICE
CERTIFICATE OF CORRECTION

PATENT NO. : 4,602,028

DATED : July 22, 1986

INVENTOR(S) : Richard C. Effland et al.

It is certified that error appears in the above-identified patent and that said Letters Patent is hereby corrected as shown below:

Column 11, line 43,
Claim No. 4 - "chorine" should be --chlorine--.

Signed and Sealed this

Twenty-fifth Day of November, 1986

Attest:

DONALD J. QUIGG

*Attesting Officer*    *Commissioner of Patents and Trademarks*